(12) United States Patent
Kuznetsov et al.

(10) Patent No.: US 9,243,886 B1
(45) Date of Patent: Jan. 26, 2016

(54) OPTICAL METROLOGY OF PERIODIC TARGETS IN PRESENCE OF MULTIPLE DIFFRACTION ORDERS

(71) Applicant: KLA-Tencor Corporation, Milpitas, CA (US)

(72) Inventors: Alexander Kuznetsov, Mountain View, CA (US); Kevin Peterlinz, Fremont, CA (US); Andrei Shchegrov, Campbell, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 28 days.

(21) Appl. No.: 13/924,204

(22) Filed: Jun. 21, 2013

Related U.S. Application Data

(60) Provisional application No. 61/664,543, filed on Jun. 26, 2012.

(51) Int. Cl.
  *G01B 9/02* (2006.01)
  *G01N 21/47* (2006.01)
  *G01N 21/956* (2006.01)

(52) U.S. Cl.
  CPC ........ *G01B 9/02083* (2013.01); *G01N 21/4788* (2013.01); *G01N 21/956* (2013.01)

(58) Field of Classification Search
  CPC ............. G01N 21/4788; G01N 21/956; G01B 9/02083
  See application file for complete search history.

(56) References Cited

U.S. PATENT DOCUMENTS

| | | | | |
|---|---|---|---|---|
| 5,777,729 A | * | 7/1998 | Aiyer | G01N 21/4788 356/237.1 |
| 5,864,394 A | * | 1/1999 | Jordan, III | G01N 21/94 257/E21.53 |
| 6,429,943 B1 | | 8/2002 | Opsal et al. | |
| 6,654,131 B2 | | 11/2003 | Opsal et al. | |
| 6,829,057 B2 | | 12/2004 | Opsal et al. | |
| 6,972,852 B2 | | 12/2005 | Opsal et al. | |
| 7,248,375 B2 | | 7/2007 | Opsal et al. | |
| 7,289,213 B2 | | 10/2007 | Mieher et al. | |

(Continued)

OTHER PUBLICATIONS

Kumar, N. et al., "Coherent Fourier Scatterometry (Tool for Improved Sensitivity in Semiconductor Metrology)", Proceedings of SPIE, vol. 8324 83240Q-1, Retrieved from the Internet: < http://spiedigitallibrary.org/ >, Accessed on Jun. 10, 2013, 2012, 8 pgs.

*Primary Examiner* — Michael A Lyons
(74) *Attorney, Agent, or Firm* — Kwan & Olynick LLP

(57) ABSTRACT

One or more non-zero diffraction orders are selected, and these selected one or more zero or non-zero diffraction orders are selected for eliminating or obtaining corresponding zero or non-zero diffraction order terms or interference term from measurements from a periodic target using an optical metrology tool. The periodic target has a pitch, and the measurements contain a zero diffraction order and one or more non-zero diffraction order terms. Using the optical metrology tool, an incident beam is directed to positions on the target, and the measurements are obtained from the target in response to the incident beam. The measurements are processed to eliminate or obtain each zero or non-zero diffraction order term or interference term associated with each selected zero or non-zero diffraction order, resulting in a processed metrology signal. The positions are shifted from each other so as to cause the zero or non-zero diffraction order term or interference term corresponding to each selected zero or non-zero diffraction order to be eliminated or obtained.

25 Claims, 5 Drawing Sheets

(56) References Cited

U.S. PATENT DOCUMENTS

| | | |
|---|---|---|
| 7,454,103 B2 | 11/2008 | Parriaux |
| 7,528,941 B2 | 5/2009 | Kandel et al. |
| 7,528,953 B2 | 5/2009 | Frommer et al. |
| 7,602,509 B1 | 10/2009 | Hench |
| 7,751,046 B2 | 7/2010 | Levy et al. |
| 2003/0212525 A1* | 11/2003 | Bischoff et al. ............... 702/127 |
| 2004/0090629 A1* | 5/2004 | Drege et al. ................... 356/445 |
| 2006/0197951 A1* | 9/2006 | Frommer et al. ............. 356/401 |
| 2006/0274325 A1* | 12/2006 | Hetzler et al. ................ 356/521 |
| 2007/0146685 A1* | 6/2007 | Yoo et al. ........................ 356/32 |
| 2007/0252986 A1* | 11/2007 | Sandstrom .................... 356/319 |
| 2008/0266548 A1* | 10/2008 | Lee et al. ......................... 356/73 |
| 2009/0225407 A1* | 9/2009 | Nakayama et al. ........... 359/370 |

\* cited by examiner

OPTICAL METROLOGY OF PERIODIC TARGETS IN PRESENCE OF MULTIPLE DIFFRACTION ORDERS

CROSS-REFERENCE TO RELATED APPLICATIONS

This application claims the benefit of U.S. Provisional Application No. 61/664,543, filed Jun. 26, 2012, by Alexander Kuznetsov et al., which application is herein incorporated by reference in its entirety for all purposes.

BACKGROUND OF THE INVENTION

The invention described herein relates generally to semiconductor metrology of a specimen, such as a wafer or reticle. More specifically, it relates to metrology that employs detection of an optical signal from a periodic target.

Generally, the industry of semiconductor manufacturing involves highly complex techniques for fabricating integrated circuits using semiconductor materials which are layered and patterned onto a substrate, such as silicon. Due to the large scale of circuit integration and the decreasing size of semiconductor devices, the device must comply with rigorous specification requirements prior to shipment of the device to the end users or customers.

Optical metrology techniques (such as spectroscopic ellipsometry, scatterometry, reflectometry, etc.) provide powerful, high-throughput capabilities for measuring critical dimensions, overlay, film thicknesses, composition, and other parameters of nanoscale structures. The measurements are often performed on targets that are in the form of repeating periodic structures, e.g., gratings. These gratings usually represent the actual device geometric and material structure or an intermediate design during device fabrication.

Although some optical metrology techniques for analyzing periodic targets work well for certain applications, it would be beneficial to provide improved mechanisms for performing metrology for periodic targets.

SUMMARY OF THE INVENTION

The following presents a simplified summary of the disclosure in order to provide a basic understanding of certain embodiments of the invention. This summary is not an extensive overview of the disclosure and it does not identify key/critical elements of the invention or delineate the scope of the invention. This summary's sole purpose is to present some concepts disclosed herein in a simplified form as a prelude to the more detailed description that is presented later.

In one embodiment, a method of obtaining optical signal measurements from a periodic semiconductor target is disclosed. The method includes selecting one or more zero or non-zero diffraction orders for eliminating or obtaining corresponding non-zero diffraction order terms or interference term from a plurality of measurements from a periodic target using an optical metrology tool. The periodic target has a pitch, and the plurality of measurements contain a zero diffraction order term and one or more non-zero diffraction order terms. Using the optical metrology tool, an incident beam is directed to a plurality of positions on the target, and the measurements are obtained from the target in response to the incident beam being directed to each position. The measurements from the positions of the targets are processed to eliminate or obtain each zero or non-zero diffraction order term or interference term associated with each selected zero or non-zero diffraction order, resulting in a processed metrology signal. The positions are shifted from each other so as to cause the zero or non-zero diffraction order term or interference term corresponding to each selected zero or non-zero diffraction order to be eliminated or obtained.

In a specific implementation, the processed metrology signal is used in a model-based metrology process for determining one or more parameters of the target. In another implementation, the processed metrology signal is used in a calibration process for the optical metrology tool. In one aspect, one or more non-zero diffraction orders are selected and the measurements are processed so that the processed metrology signal retains only zero diffraction terms and eliminates non-zero diffraction order terms corresponding to the selected one or more non-zero diffraction orders. In another aspect, one or more non-zero diffraction orders are selected and the measurements are processed so that the processed metrology signal retains only zero diffraction terms and separated one or more non-zero diffraction order terms corresponding to the selected one or more non-zero diffraction orders, while eliminating interference terms corresponding to the selected one or more non-zero diffraction orders. The measurements are electric field measurements, and the measurements are processed so that the processed metrology signal is equal to an average of the electric field measurements from the positions. In one aspect, the electric field measurements are obtained in the near-field portion of the optical metrology system. In another aspect, the electric field measurements are obtained in the far-field portion of the optical metrology system. In another implementation, the measurements are intensity measurements, and the measurements are processed so that the processed metrology signal is equal to an average of the intensity measurements from the positions.

In another embodiment, each relative shift between the positions is selected based on the selected one or more non-zero diffraction orders, while an absolute value for each position is unspecified. In one aspect, the positions are shifted with respect to each other by a rational fraction of the pitch based on the selected one or more non-zero diffraction orders. In a detailed example, the measurements include a spatial average of a plurality of sub-measurements for each position. In another example, the target comprises gratings arranged in two directions. In a specific implementation, the measurements are obtained using a plurality of incident beams directed simultaneously to at least two of the positions.

In one embodiment, the measurements are processed so that the processed metrology signal retains only zero diffraction terms and one or more non-zero diffraction order terms not corresponding to the selected one or more diffraction orders and eliminates non-zero diffraction order terms corresponding to the selected one or more diffraction orders. In one aspect, the measurements are processed so that the processed measurement signal retains an individual interference term corresponding to one of the selected one or more diffraction orders and such individual interference term is retained by comparing the plurality of measurements to each other.

In an alternative embodiment, the invention pertains to an apparatus for obtaining optical signal measurements from a periodic semiconductor target. The apparatus includes a measurement module for directing an incident beam towards a periodic target having a pitch and a detection module for obtaining measurements having multiple diffraction orders from the periodic target in response to the incident beam. The apparatus further comprises a processor that is configured to perform one or more of the above described method operations.

These and other features of the present invention will be presented in more detail in the following specification of embodiments of the invention and the accompanying figures which illustrate by way of example the principles of the invention.

DETAILED DESCRIPTION OF SPECIFIC EMBODIMENTS

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with the specific embodiments, it will be understood that it is not intended to limit the invention to the embodiments.

INTRODUCTION

Figure 1:
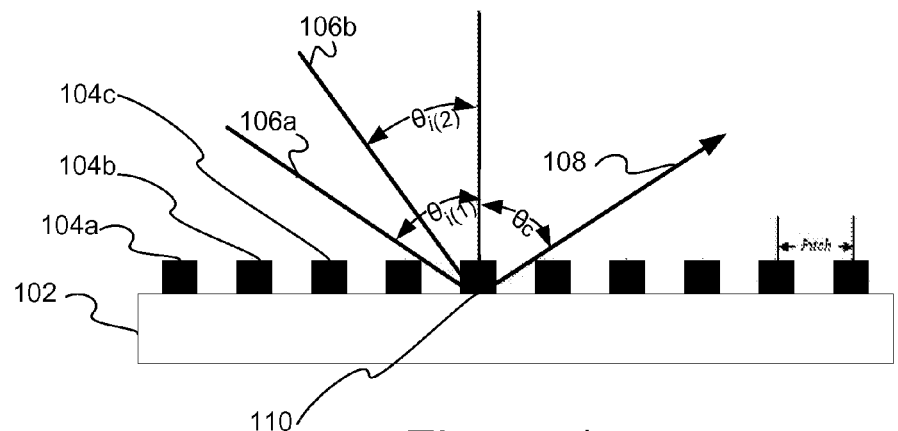
FIG. 1 illustrates a simplified beam profile reflectometry (BPR) example having two rays of a probe beam at two different angles of incident focused onto a same position of a grating.

A beam profile reflectometry (BPR) example will first be described to illustrate challenges with processing optical signals having multiple diffraction order content. In a BPR system, a probe beam can be focused with a strong lens so that the rays within the probe beam strike a target at multiple angles of incidence. FIG. 1 illustrates a simplified BPR example having two rays of a probe beam at two different angles of incident focused onto a same position 110 of a grating target formed from line structures, e.g., lines 104a, 104b, and 104c, having a specific pitch disposed on substrate 102. As shown, first ray 106a has an angle of incidence $\Theta_{i(1)}$, while second ray 106b has an angle of incidence $\Theta_{i(2)}$.

The angle-resolved intensity of the reflected beam 108 can be measured, for example, by an array photodetector. However, this reflected beam 108 sometimes includes not only the specularly reflected light, but also the light that has been scattered into that detection angle from non-specular diffraction orders. For example, using multiple angles of incidence for particular wavelength ranges, e.g., lower wavelengths, may tend to cause more interference terms in the reflected signal. The collected signal $\sin(\Theta_c)$ 108 can include a contribution from the first ray 106a related to $\sin(\Theta_{i(1)})$, as well as a contribution from the second ray 106b related to $\sin(\Theta_{i(2)})$+ $m\lambda$/pitch, where m is the diffraction order. Thus, the radial positions of the rays in the beam impinging on the detector may correspond to different angles of incidence on the sample plus the integrated scattering from all of the angles of incidence contained in the incident beam.

One analysis goal may include fitting the measured reflected intensity to various sample characteristics, such as grating dimensions and composition, via modeling techniques. However, there are several challenges in performing such model-to-data fitting in the presence of multiple diffraction orders. If the measured signal contains components caused by interference between multiple diffraction orders, the model for such detected intensity would need to include a quantitative description of the interference between multiple orders and, thus, the relative phase for the corresponding illumination field terms for any given collection angle, which contains contributions from multiple diffraction orders. Similarly, since the relative phases for all orders, other than zero order, change with the relative position of the periodic structure with respect to the illumination field, the model for fitting to detected signals having interference terms would also need to include a quantitative description of the sample position dependence for phases from different orders and the measurement position would have to be accurately determined.

Additionally, intensity measurements (or other types of measurements) include multiple diffraction orders and interference terms may not only depend on the particular location of the beam spot on particular gratings, but also may depend on the grating pitch. For instance, larger pitch gratings tend to result in greater position dependent sensitivity.

In one modeling example, electromagnetic computational algorithms, such as RCWA (rigorous coupled wave analysis), may be used to compute light propagating with separate diffraction orders, including non-propagating (evanescent) orders, from a particular grating having variable characteristics (such as shape and composition). Although goal is to fit the detected data to the output of the model so as to determine the characteristics of the grating under test, the ability to calculate separate diffraction orders is not sufficient to accurately or reliably fit measured data due to the challenges of interference, position dependence, and normalization. That is, an RCWA technique does not account for interference terms in detected data and cannot be used with detected data having multiple interfering orders.

Another modeling technique is finite element modeling (FEM). FEM computes local field patterns or finite sized (spot) illumination profiles with all diffraction orders, even evanescent orders. However, the relative phase between interference or order terms would still depend on the measurement position on the grating. Since accurately measuring grating position tends to be difficult, it is also difficult to account for such position in an FEM data-fitting process in the presence of multiple diffraction orders.

The difference in the measured signal for different locations on a grating can also hinder calibration of the metrology tool when measurements include multiple diffraction orders that cause complex interference issues. In this case, the calibration for each metrology tool is not only dependent on the particular optics of the tool, but is also dependent on the position on the grating, as well as the grating pitch.

A very accurate measurement for the incident beam position with respect to each particular grating would need to be used for model-based target analysis and calibration of measured signals that have multiple diffraction interference terms that are position dependent. An increase in the measurement accuracy entails an increase in the complexity of the stage movement and coordinate system mechanism of the metrology tool. Such accuracy may be impractical in some metrology systems.

In view of the above challenges, one option is to use a grating that allows for selection of single diffraction $-1^{st}$ order. However such a grating removes the zero order and all other orders, thereby, significantly reducing the amount of useful information. This type of grating is also not very practical for semiconductor metrology, in which grating design is guided primarily by semiconductor device fabrication design rules Another option may be to use multiple diffraction orders in a non-model-based application, such as overlay metrology. However, as mentioned before, a model-based metrology is useful for a diverse number of applications as described further herein.

Model-Based Metrology Using Multiple Diffraction Orders

In general, certain embodiments of the present invention facilitate the processing of optical metrology signals that have one or more non-zero diffraction orders and are obtained from a periodic target having a particular pitch, such as a grating structure. In one embodiment, undesirable non-zero diffraction orders or interference terms that depend on the position of the illumination beam on the target are suppressed, or, alternatively, specific interference terms can be obtained as described further herein.

Suppression of specific diffraction orders or interference terms may be achieved by processing signals from multiple measurements on the target at specific relative locations. In certain embodiments, separated signal components for specific multiple diffraction orders may be obtained, while removing interference terms. Measured signals having non-zero diffraction orders can be processed and used, while eliminating the undesirable interference effect of interference caused by selected non-zero diffraction orders, by taking measurements at specific relative grating locations.

Either the grating target or the illumination beam can move for each new target location or the grating target and the illumination beam can move at the same time so as to obtain measurements at locations on the target that are specified distances apart as described further herein. Alternatively, multiple incident beams can be generated and directed simultaneously towards a plurality of target locations.

Measured signals that are processed so as to suppress specific interference terms from multiple diffraction orders can be utilized for any number of applications. For instance, enhancement or suppression of particular of signals with desirable diffraction order content can be used for model-based critical dimension, overlay, or other target property metrology for semiconductor industry fabrication applications. Enhancement or suppression of particular of signals with desirable diffraction order content can also be used to calibrate a particular metrology tool for different types of gratings, even gratings that produce multiple diffraction orders across the pupil plane. Various processed enhanced or suppressed signals can be determined and compared to each other so as to determine specific interference terms, which may be used for various analysis applications.

In one embodiment, a measured electric field signal from selected relative target positions may be processed to eliminate selected non-zero diffraction orders from the processed signal. In certain embodiments, target positions are shifted with respect to each other by $$x_0 + \frac{\text{Pitch}}{2m}$$

and such measurements are averaged together to eliminate each selected $m^{th}$ order. If the $1^{st}$ order is present and is selected to be eliminated, the target can be measured at two target positions $$x_0 \text{ and } x_0 + \frac{\text{Pitch}}{2},$$

and the measured electric field from such positions can be averaged together so that $1^{st}$ diffraction order is eliminated. If electric field measurements still had other diffraction orders present, those other orders, in addition to the $0^{th}$ order, would remain present in the measured signals. If $0^{th}$, $1^{st}$, $2^{nd}$ and $3^{rd}$ orders were present and the $1^{st}$ order is selected to be eliminated, averaged measurements from positions $$x_0 \text{ and } x_0 + \frac{\text{Pitch}}{2}$$

would result in eliminating the $1^{st}$ order, while maintaining the $0^{th}$, $2^{nd}$, and $3^{rd}$ orders, for example. When 0, $1^{st}$, and $2^{nd}$ orders are present and $1^{st}$ and $2^{nd}$ are selected to be eliminated, the target can be measured at four target positions:

$$x_0, x_0 + \frac{\text{Pitch}}{4},$$

$$x_0 + \frac{\text{Pitch}}{2}, \text{ and } x_0 + \frac{3 \text{ Pitch}}{4}.$$

In this latter example, each measurement position is shifted by $$\frac{\text{Pitch}}{4}.$$

Alternatively, the $2^{nd}$ order may simply be eliminated and the $0^{th}$, $1^{st}$, and $3^{rd}$ orders retained by measuring target positions $$x_0 \text{ and } x_0 + \frac{\text{Pitch}}{4}$$

The following Equation [1] can be used to average out all non-zero diffraction order terms that are present and leave only the $0^{th}$ order term in an electric field measurement system having a particular number of non-zero diffraction orders present:

$$E_{av}(x) = \frac{1}{2m} \sum_{i=0}^{2 \cdot m - 1} E_{refl}\left(x + \frac{i}{2m} \text{Pitch}\right) \quad \text{Equation [1]}$$

wherein m is the highest diffraction order present in the system. Using Equation [1], non-zero diffraction orders can also be eliminated from the far field by averaging electric field measurements obtained over specific relative target positions in the near field.

The $0^{th}$ order may also be selectively removed. The main application for removing $0^{th}$ order would be overlay metrology (which typically uses only $+/-1^{st}$ orders), but such $0^{th}$ order removal can also be used in CD metrology as well. The elimination of $0^{th}$ order can be accomplished by any suitable technique. If the output signal includes $0^{th}$, $1^{st}$, and $2^{nd}$ orders, then two measurements may be obtained. In the first measurement, $2^{nd}$ order is removed, so $0^{th}$ and $1^{st}$ are left. In the second measurement, $1^{st}$ and $2^{nd}$ order are removed so only $0^{th}$ order is left. Finally, the difference between these two measurements will produce the signal containing $1^{st}$ order only.

Figure 2:
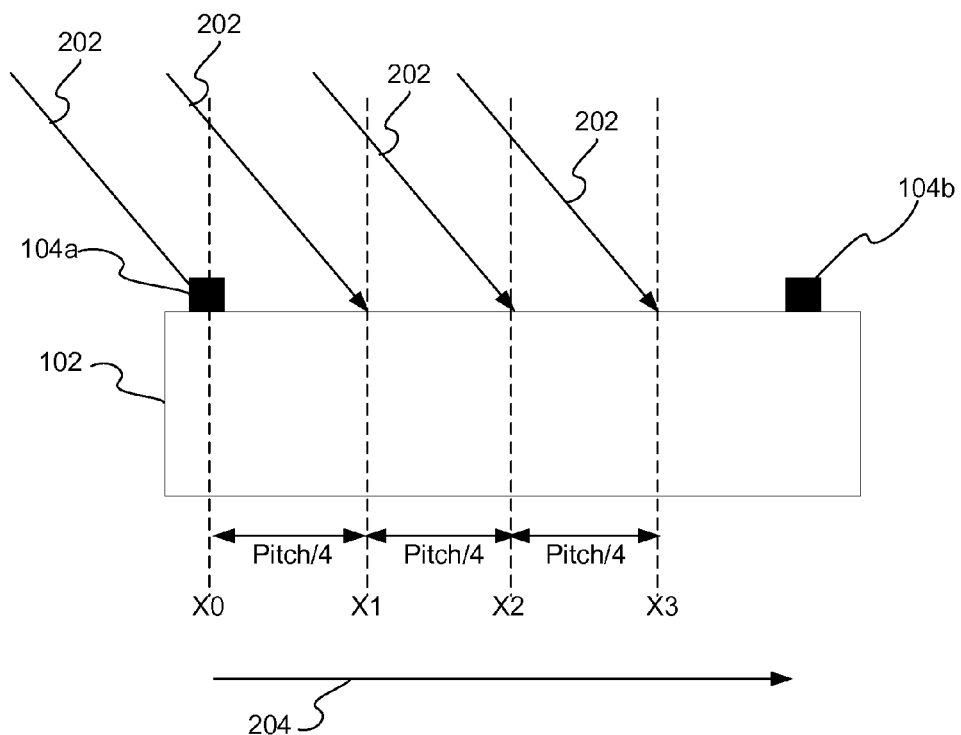
FIG. 2 is a diagrammatic side view of a grating target that is undergoing metrology at multiple grating positions in accordance with a first example implementation of the present invention.

FIG. 2 is a diagrammatic side view of a grating target that is undergoing metrology at multiple grating positions in accordance with a first example implementation of the present invention. As shown, the grating includes structures 104a, 104b, and 104c on substrate 102. This structures 104a-104c form a grating having a specific pitch.

Incident beam 202 is directed towards position X0 at which a measurement is obtained. For example, the electric field that results from the incident beam 202 at position X0 is measured. The incident beam 202 is also directed to a position X1 that is a distance of pitch/4 from position X0. For instance, incident beam 202 is moved in direction 204. Likewise, the incident beam 202 can then be moved sequentially to positions X2 and X3. Alternatively, more than one incident beam can be directed simultaneously towards to two or more positions, and an electric field can be measured for each position. The four different electric field measurements are then averaged together to result in an average electric field value from which $1^{st}$ and $2^{nd}$ order diffraction orders have been removed.

Averaging electric field measurements from the relative positions specified in Equation [1] results in cancellation of the corresponding diffraction order terms in the processed result. In a simple 0 and $1^{st}$ order example, the average of the electric field for two positions X0 and X0+pitch/2 are given by:

$$E(x=X0)=E_0+E_1$$

$$E(x=X0+\text{Pitch}/2)=E_0-E_1$$

Accordingly, averaging these electric fields together results in:

$$E_{av}=(E_0+E_1+E_0-E_1)/2 \text{ or simply } E_0.$$

Figure 3:
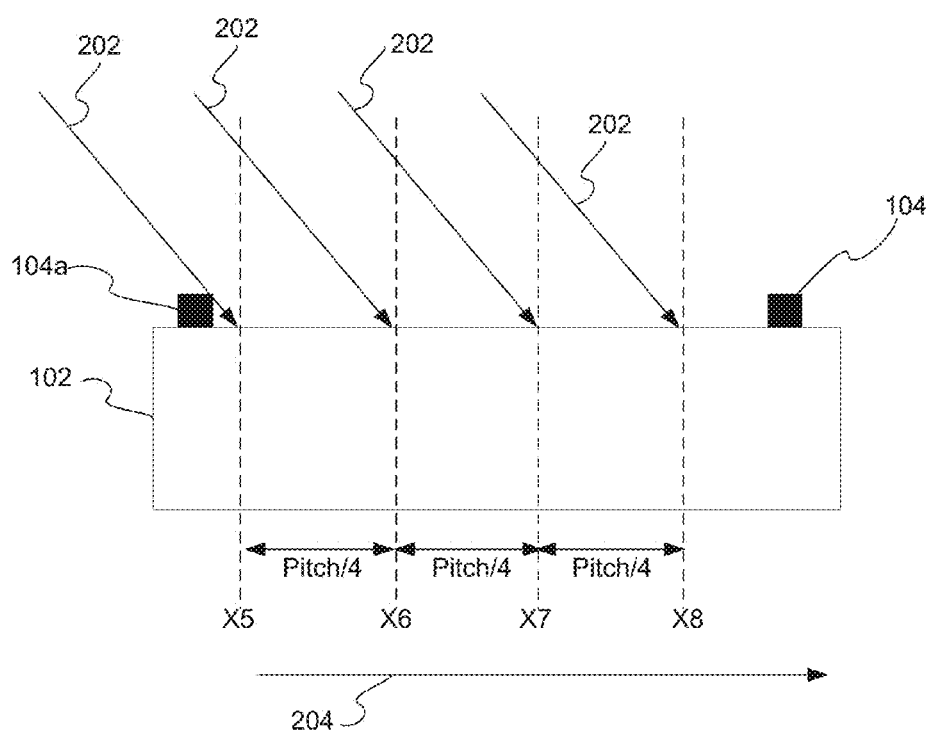
FIG. 3 is a diagrammatic side view of a grating target that is undergoing metrology at multiple grating positions in accordance with a second example implementation of the present invention.

Certain absolute positions of the incident beam with respect to the grating do not have to be chosen in order to effectively eliminate non-zero diffraction order contributions. For example, the techniques described herein will work by processing measurement signals from any absolute initial grating position, as long as specific relative grating positions are selected and used. FIG. 3 is a diagrammatic side view of a grating target that is undergoing metrology in accordance with a second example implementation of the present invention. As shown, a signal is measured or collected from alternative positions X5, X6, X7, and X8, which differ from the positions of FIG. 2. Both sets of measurement positions would result in elimination of the $1^{st}$ and $2^{nd}$ diffraction order interference terms from an averaged measured signal.

Eliminating diffraction orders from an averaged electric field can be accomplished using either local fields (fields close to the grating) or far fields (fields close to the objective or detector). Due to the nature of local to far field transformation, such averaging techniques would yield the same result. The important implication of this result is that in the real system, such diffraction order elimination can be done in any part of the optical system. For example, local field mixing can be done using specially designed objective, while far field mixing can be done on the detector side. These implications are further described in the above-referenced U.S. Provisional Application No. 61/664,543.

Figure 5:
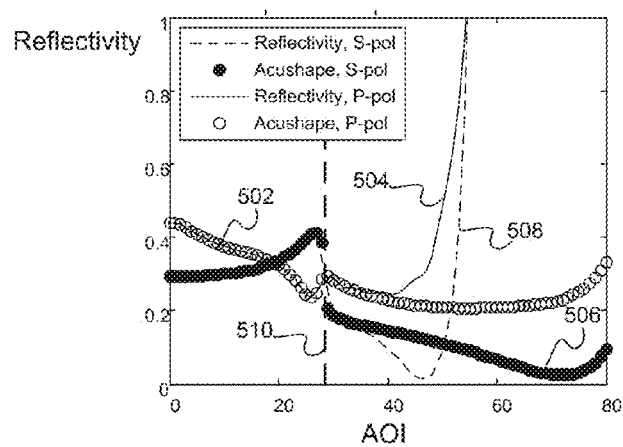
FIG. 5 is a graph of reflectivity values as a function of angles of incidence (AOI) without averaging of electric field measurements.

FIG. 5 is a graph of reflectivity values as a function of angles of incidence (AOI) at 355 nm wavelength without averaging of electric field measurements. The values of dotted line 508 correspond to reflectivity measurements with S polarization having $1^{st}$ order interference terms, while the solid line 504 corresponds to reflectivity measurements with P polarization having $1^{st}$ order interference terms. The corresponding simulation results for $0^{th}$ order reflectivity of S and P polarizations from AcuShape® software available from KLA-Tencor of Milpitas, Calif. are plotted using solid circles 506 and open circles 502, respectively. As shown, measurement results, which are not averaged, would tend to deviate substantially from the simulated results for an AOI value greater than about 29°. This deviation is caused by $1^{st}$ order diffraction interference. That is, the $0^{th}$ and $1^{st}$ orders are present and not separated in the far field R values, and model for producing the simulation results does not account for the $1^{st}$ diffraction order term.

Figure 6:
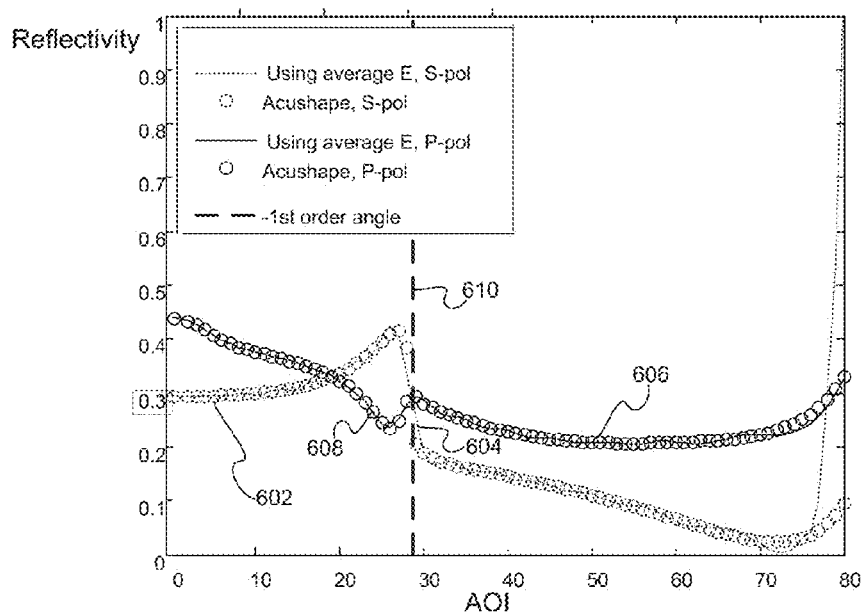
FIG. 6 is a graph of reflectivity values as a function of angles of incidence (AOI) that illustrates removal of $1^{st}$ diffraction order effects by averaging of electric field measurements in accordance with embodiments of the present invention.

The $1^{st}$ order can be eliminated by averaging electric field measurements at positions that are shifted by pitch/2 as described herein. FIG. 6 is a graph of reflectivity values as a function of angles of incidence (AOI) at 355 nm wavelength that illustrates removal of $1^{st}$ diffraction order effects by averaging of electric field measurements in accordance with embodiments of the present invention.

Any suitable metrology tool may be used to measure and process electric field measurements from specific relative target positions. An example system is an interferometer system, which is capable of producing multiple incident beams on the target grating. Specific examples include a Michelson interfereometer, a Mach-Zehnder interferometer, and a Sagnac interferometer. In general, a metrology tool that can obtain electric field measurements can be either configured to measure both intensity and phase or configured to spatially separate multiple, spatially coherent illumination beams on the sample and provide phase-corrected recombination of the collected beams. Multiple illumination beams can have also be separated by additional multiple integrals of grating pitch, for example, in order to ensure such separation exceeds the diffraction limit.

In certain metrology systems, intensity measurements are more accessible. Working with the intensity of the far field, rather than with the electric field itself, can be much simpler. Moreover, current systems, including BPR, SE and eUVR, all measure light intensity and not electric field.

Additionally, if intensity measurements from specific relative positions are averaged, non-zero diffraction order terms can be retained and separated, while removing only the non-zero diffraction interference terms. This result can be illustrated for a system in which the $0^{th}$ and $1^{st}$ orders are present and measurements are obtained for grating positions X0 and X0+pitch/2. The average intensity (I) for these positions can be expressed as follows:

$$I = \frac{1}{2}\left[|E(x = X0)|^2 + \left|E\left(x = X0 + \frac{\text{Pitch}}{2}\right)\right|^2\right]$$

$$I = |E_0|^2 + |E_1|^2$$

Accordingly, only incoherent addition of separated $0^{th}$ and $1^{st}$ order terms are maintained, while interference terms caused by the $1^{st}$ order are eliminated. Likewise, if multiple diffraction orders exist in the system, multiple diffraction order interference terms can be eliminated, while maintaining the individual diffraction order terms as shown by the following:

$$I = \frac{1}{2m}\sum_{j=0}^{2*m-1}\left|E\left(X0 + \frac{j}{2m}\text{Pitch}\right)\right|^2 = \sum_{j=0}^{m}|E_j|^2$$

where m equals the highest diffraction order and j equals the diffraction order number, starting at the $0^{th}$ diffraction order). In sum, intensity signals can be combined over several positions of the grating so as to, for example, eliminate position-dependent interference from processed intensity signals. In this implementation, multiple diffraction orders can be retained and used. In general, the metrology recipe is selected to collect data at points separated by a rational fraction of the pitch (e.g., pitch/4, pitch/4, 3*pitch/4, etc.). More generally, an intensity average that separates diffraction orders, while eliminating interference terms, can be determined by the following Equation [2]:

$$I = \frac{1}{2m}\sum_{i=0}^{2*m-1}I\left(X0 + \frac{i}{2m}\text{Pitch}\right) \quad \text{Equation [2]}$$

Intensity interference terms can be selectively separated and used. Such separation can be done by analyzing a difference between two signals containing multiple diffraction orders. For example, the interference term between $0^{th}$ and $1^{st}$ orders can be obtained by comparing two signals shifted by Pitch/2 from each other as shown below in Equation [3]:

$$\Delta I = I(X0) - I\left(X0 + \frac{\text{Pitch}}{2}\right) = 2(E_0 E_1^* + E_1 E_0^*) \quad \text{Equation [3]}$$

In a more general case, when m diffraction orders are present, the interference term between the $i^{th}$ ($0<i\leq m$) order and the other orders can be obtained by $$\Delta I_i = I(X0) - I\left(X0 + \frac{\text{Pitch}}{2i}\right)$$

Interference terms also contain information about relative phase between different diffraction orders and, accordingly, interference terms can be used in addition to an absolute intensity signal. One of the possible examples of using interference term is obtaining pitch of the target by continuously scanning along the target and analyzing periodicity of measured interference data.

In some cases, a spatial average may be taken around each measurement point to obtain robust data and make such measurements less sensitive to local profile variations, e.g., caused by roughness and other factors. For instance, the measurement recipe can be modified to process data with spatial averaging around the first measurement location on the target and a shifted location or shifted locations, also with spatial averaging around those one or more shifted locations.

Any of the techniques described herein can also be extended to bi-periodic grating targets with different periods in two directions. The directions do not have to be orthogonal to each other. Additionally, other types of periodic targets, besides line gratings, may be used with the techniques of the present invention. Alternative periodic structures include periodic grids, rectangles, squares, curved lines, curved shapes, circles, cylindrical shapes, conical shapes, etc., or combinations of the foregoing. Additionally, the term "grating" is used herein to refer to any type of periodic target.

Figure 4:
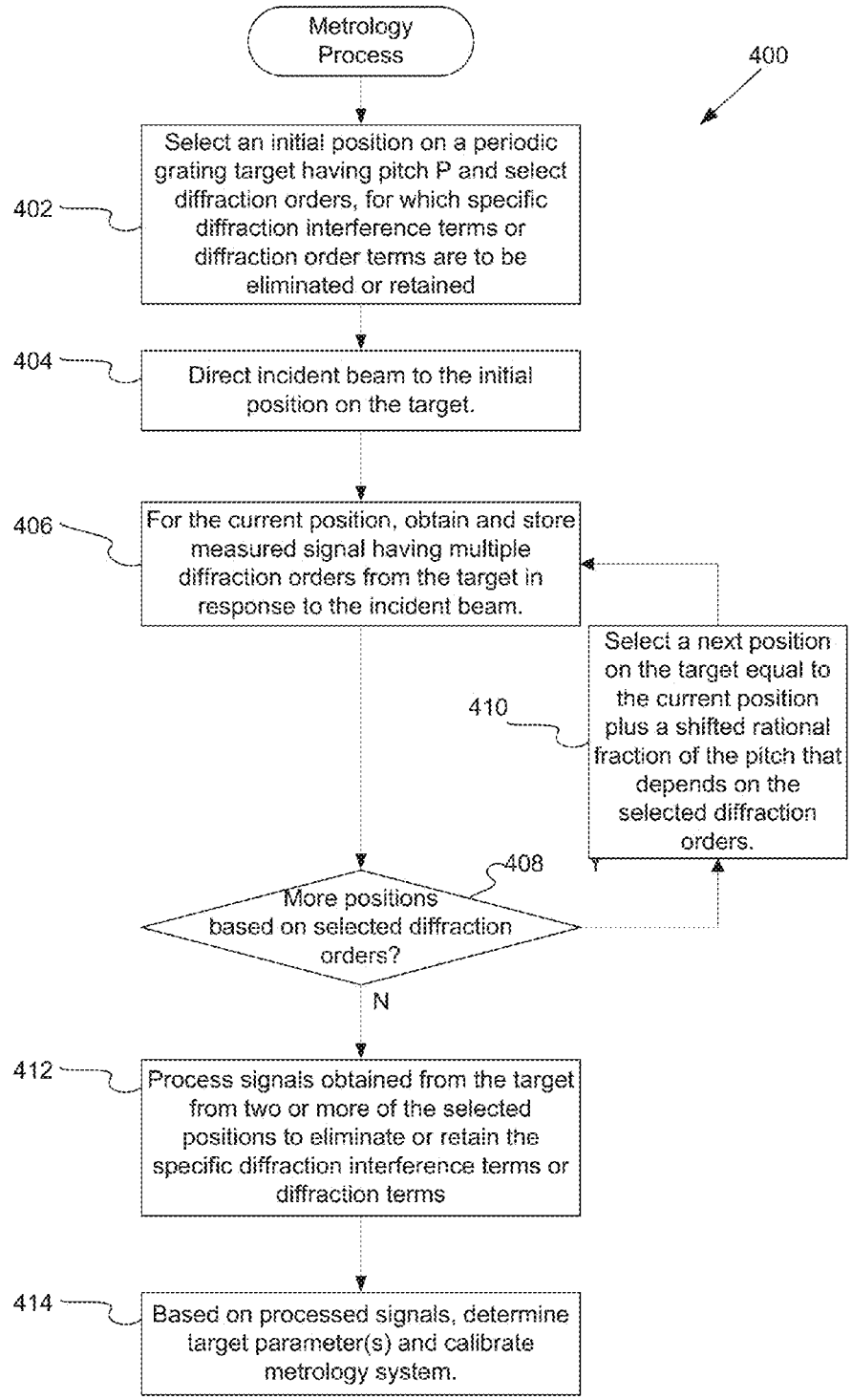
FIG. 4 is a flow chart illustrating a metrology procedure in accordance with one embodiment of the present invention.

Any suitable technique may be implemented to obtain a processed measurement signal from specific locations of a periodic target in order to eliminate non-zero diffraction order terms or only interference terms (while separating diffraction orders) from such processed signal. FIG. 4 is a flow chart illustrating a metrology procedure 400 in accordance with one embodiment of the present invention. The method includes selecting an initial position on a grating target having pitch P and selecting diffraction orders, for which specific diffraction interference terms or diffraction order terms are to be eliminated or retained, in operation 402.

For instance, a specific set of operating parameters on a metrology tool for performing metrology on a specific grating target (or the like) is set up (e.g., via a recipe). Certain combinations of operating parameters and target parameters can be predicted to result in multiple diffraction orders in the measured signal. A set of target positions may be selected so as to cancel or enhance specific diffraction order terms that are predicted to be present.

The incident beam of the optical tool may be then directed to the initial position on the target in operation 404. Any initial grating position may be used. For the current position, a measured signal having multiple diffraction orders (if present) may be obtained and stored in response to the incident beam impinging on its current grating position (initial or next shifted position) in operation 406. It may then be determined whether there are more positions based on the selected diffraction orders in operation 408. If there are more positions, a next position on the target equal to the current position plus a rational fraction of the pitch, which depends on the selected diffraction orders, is selected in operation 410. By way of examples, next positions may be selected based on the selected diffraction orders to be eliminated as specified by Equation [1] for electric field measurements or Equation [2] for intensity measurements.

Although the techniques of the present invention are described herein as utilizing specific types of measured signals (e.g., electric field or intensity measurements) from a plurality of target positions, any suitable type of measurable signal obtained from a periodic target may be used to practice the techniques of the present invention. Example signals include, but are not limited to, any type of spectroscopic ellipsometry or reflectometry signals, including: $\Psi$, $\Delta$, Rs (complex reflectivity of the s polarization), Rp (complex reflectivity of the p polarization), Rs ($|r_s|^2$), Rp ($|r_p|^2$), R (unpolarized reflectivity), $\alpha$ (spectroscopic "alpha" signal), $\beta$ (spectroscopic "beta" signal), and functions of these parameters, such as tan($\Psi$), cos($\Delta$), ((Rs−Rp)/(Rs+Rp)), etc. The signals could alternatively or additionally be measured as a function of incidence angle, detection angle, polarization, azimuthal angle of incidence, detection azimuthal angle, angular distribution, phase, or wavelength or a combination of more than one of these parameters. The signals could also be a characterization of a combination of signals, such as an average value of a plurality of any of the above described ellipsometry and/or reflectometry signal types. Other embodiments may use monochromatic or laser light sources where at least one of the signals may be obtained at a single wavelength instead of at multiple wavelengths. Techniques for selecting diffraction orders in the output beam are also applicable to measurements with different types of photon sources, including optical (deep UV, UV, visible, IR) and X-ray or EUV sources (since the electromagnetic field description holds for all these wavelength ranges).

After measurements are obtained and stored for two or more selected positions, these signals can then be processed to eliminate or retain specific diffraction interference terms or diffraction order terms in operation 412. Alternatively, averages may be calculated as each set of measurements are obtained. By way of examples, an average electric field measurement is obtained as specified by Equation [1] for electric field measurements or Equation [2] for intensity measurements. Alternatively, specific interference terms may be obtained by comparison of results from appropriate one or more grating positions.

Based on the processed signals, one or more target parameters may be determined and a metrology system may be calibrated in operation 414. Target parameters, such as shape or composition, may be determined by inputting the processed measurement results from the target into a model that outputs target parameters. Suitable modeling software includes AcuShape®, available on the SpectraShape 9000, SpectraShape 8000 Series, SpectraCD-XT$_R$, or SpectraCD 200 metrology tools from KLA-Tencor of Milpitas, Calif. Example target parameters that can be determined based on a suitable modeling technique and one or more processed measured signal include critical dimension (CD), film thickness, metal gate recess, high k recess, side wall angle, step height, pitch walking, trench and contact profile, overlay, material properties (e.g., material composition, refractive index, stress on critical films, including ultra-thin diffusion layers, ultra-thin gate oxides, advanced photoresists, 193 nm ARC layers, ultra-thin multi-layer stacks, CVD layers, and advance high-k metal gate (HKMG), ultra-thin decoupled plasma nitridation (DPN) process layers, stress on noncritical films, including inter-dielectrics, photoresists, bottom anti-reflective coatings, thick oxides and nitrides, and front and back end of line layers), semiconductor manufacturing process parameters (e.g. focus and dose for scanners, etch rate for etching tools), etc.

Eliminating the interference terms by processing measured intensity signals, for example, from specific relative target positions allows increased sensitivity to be achieved due to the presence of multiple separated diffraction orders in the processed signal, e.g., in angle-resolved scatterometry using coherent illumination. In this case, the processed signal no longer contains position dependent interference terms and can be used with more comprehensive modeling techniques that incorporate diffraction orders so as to characterize or calibrate with various types of gratings, such as higher pitch gratings, under a wider range of measurement parameters, such as lower wavelengths and larger angles of incidence.

The processed metrology signals produced by techniques of the present invention may also be used for calibration. In order to use a signal containing multiple diffraction orders for other applications, such as model-based metrology, proper normalization is first performed on the particular metrology tool so that such tool's results are calibrated to match the results for a known reference target. Normalization usually involves using the particular metrology tool to obtain measurements on a reference target, such as a silicon target, an aluminum target, or a thin-film target, and then using the reference measurements to factor out contributions that depend on the illumination profile, optical system imbalances, etc.

Calibration changes from tool to tool. That is, different metrology tools will measure different signal values at the detector or the like. If X photons counts were measured from a known target having known reflectivity of 0.5, then X/2 photon counts measured on an unknown target would be calibrated to calculate a reflectivity of 0.25. Calibration could be performed for various optical tool properties, such as for each detector pixel.

Usually, normalization procedures consider only specular reflection of a substrate. However, these procedures can be modified to consider non-specular reflection as well.

In a simple calibration example, a 2D grating with NA→1 and 0 azimuth angle is considered. During a typical calibration process, $I_{in}$ is the intensity of incoming light; $I_{out}$ is the intensity measured at the detector; and $\alpha$ is the angle of incidence. $I_{in}$ can be found by measuring some reference wafer having known target, from which a known reflectivity value can be simulated. This normalization method leaves $I_{in}$ unchanged.

In the presence of high diffraction orders, $I_{out}$ is $$I_{out}(\alpha) = \sum_m I_{in}\left(\sin^{-1}\left(\sin(\alpha) + \frac{m\lambda}{d}\right)\right) \cdot R_m\left(\sin^{-1}\left(\sin(\alpha) + \frac{m\lambda}{d}\right)\right),$$

where $\lambda$ is the wavelength, d is the grating pitch, and $R_m$ is the reflectivity coefficient of $m^{th}$ diffraction order. The sum is over all integer m such that $$\left|\sin(\alpha) + \frac{m\lambda}{d}\right| \leq 1.$$

In the above equation for $I_{out}(\alpha)$, $I_{out}(\alpha)$ and $I_{in}(\alpha)$ may be obtained by measuring sample and reference targets, respectively. Coefficients $R_m^{th}(\alpha)$ at $m \neq 0$ can then be pre-computed. The reflectivity of an unknown target can then be calibrated based on:

$$R_0(\alpha) = \frac{I_{out}(\alpha) - \sum_{m \neq 0} I_{in}\left(\sin^{-1}\left(\sin(\alpha) + \frac{m\lambda}{d}\right)\right) \cdot R_m^{th}\left(\sin^{-1}\left(\sin(\alpha) + \frac{m\lambda}{d}\right)\right)}{I_{in}(\alpha)}$$

The above equation for calibrating the reflectivity of an unknown sample is valid for incoherent addition only. To get rid of coherent terms in intensity, intensity measurements can be averaged over multiple measurements at several grating positions according to the above described Equation [2].

This calibration technique allows for the separation of all non-zero diffraction orders. Accordingly, the entire pupil area can be used independently of the contamination by non-zero orders.

Several of the techniques of the present invention may be implemented using any suitable combination of software and/or hardware system. For example, the techniques may be implemented within an overlay or CD metrology tool. Preferably, such metrology tool is integrated with a computer system which implements many of the operations of this invention. Such composite system preferably includes at least an illumination module for obtaining optical measurement signals of the targets, a detection module for obtaining measurements signals from the targets, and a processor configured to analyze the obtained measurement signals to thereby determine properties of such targets or to calibrate the metrology system. At a minimum, the illumination module will usually include a source of illumination oriented to direct radiation onto specified locations of the target and the detection module will include one or more detectors oriented to detect measurement signals, which has been emitted from the target in response to the illumination.

Regardless of the system's configuration, such a metrology tool may employ one or more memories or memory modules configured to store data, program instructions for the general-purpose inspection operations and/or the inventive techniques described herein. The program instructions may control the operation of an operating system and/or one or more applications. The memory or memories may also be configured to store measurement or diffraction data, modeling algorithms, target parameter results, calibration results, etc.

Because such information and program instructions may be employed to implement the systems/methods described herein, embodiments of the present invention relates to machine readable media that include program instructions, state information, etc. for performing various operations described herein. Examples of machine-readable media include, but are not limited to, magnetic media such as hard disks, floppy disks, and magnetic tape; optical media such as DVD or CD disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Figure 7:
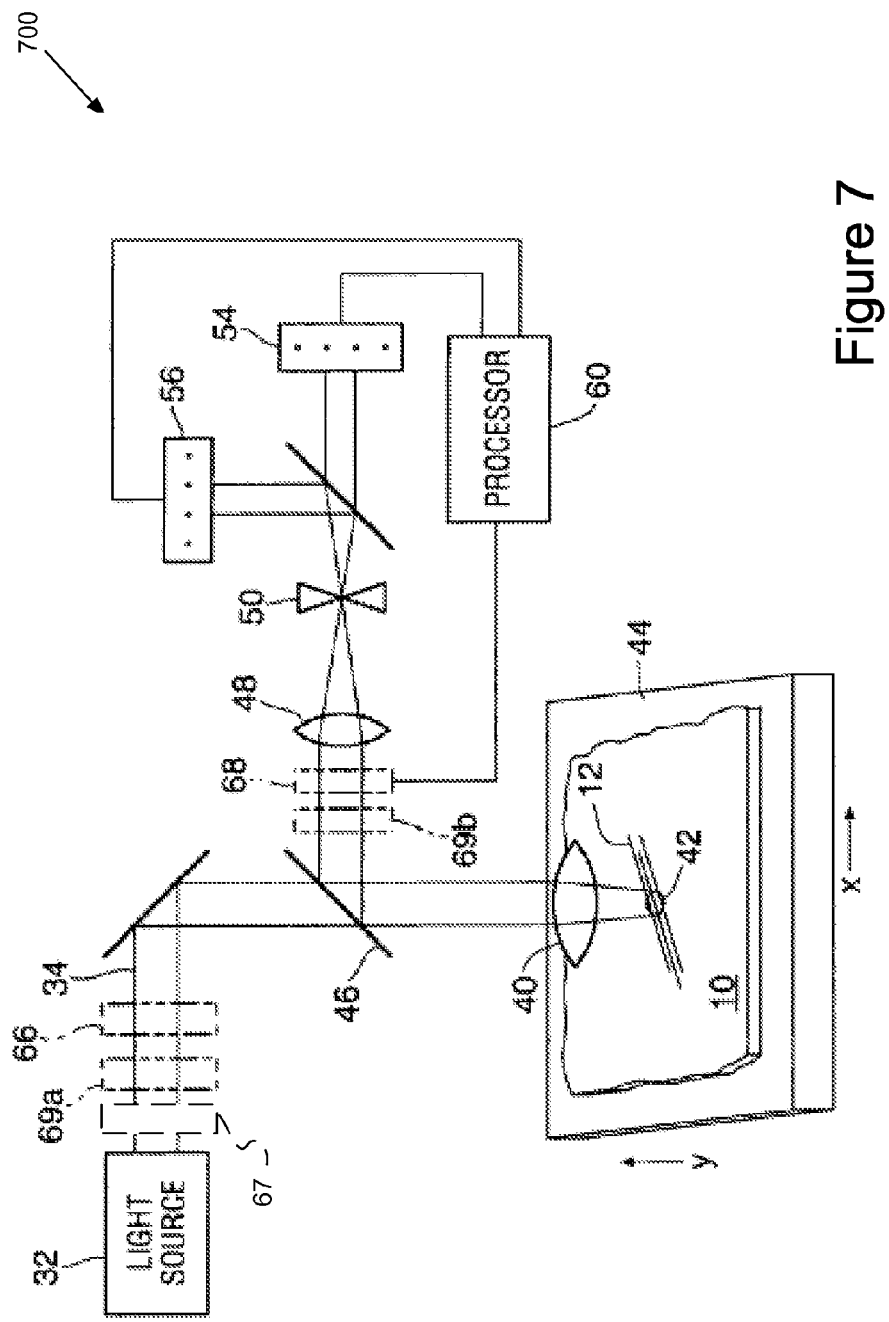
FIG. 7 is a basic schematic of a simultaneous multiple angle of incidence apparatus in which periodic targets of the present invention may be measured

FIG. 7 is a basic schematic of simultaneous multiple angle of incidence apparatus 30 in which periodic targets of the present invention may be measured. Further details about such a device and techniques for analyzing measurement results are further described in U.S. Pat. Nos. 7,248,375; 4,999,014; 5,042,951; 5,159,412; and 5,412,473, which these patents are incorporated herein by reference. The basic measurement system includes a light source 32 for generating a probe beam 34. The light source can be a laser for generating a coherent beam of radiation. Laser diodes are suitable laser sources for this application. If the output of the laser is not itself polarized, a separate linear polarizer can be provided. Light source 32 can also be a polychromatic or white light source for generating a probe beam with a plurality of wavelengths.

The probe beam 34 is focused onto the target 12 on sample 10 using a lens 40 in a manner so that the rays within the probe beam create a spread of angles of incidence. In one embodiment, the beam is directed normal to the surface but can be arranged off-axis as illustrated in U.S. Pat. No. 5,166,752, incorporated herein by reference. Lens 40 is preferably a high numerical aperture lens (on the order of 0.90) to create angles of incidence from zero to about 70 degrees. The lens creates rays having predominantly S-polarized light along one axis and predominantly P-polarized light along an orthogonal axis. At intermediate angles, the polarization is mixed.

Lens 40 is positioned to create a probe beam spot 42 on the sample on the order of about 1 micron in diameter where the light source is coherent (e.g., a laser source). This spot can typically be somewhat larger than the spacing (width W) between the recurring features of the periodic structure. For this reason, a certain portion of the light from the probe beam will be diffracted or scattered from the periodic structure. As discussed herein, this light data can be analyzed with a scattering model in a manner similar to prior art probe beam detection scatterometry systems. The light data can be simultaneously obtained from a plurality of angles of incidence.

The target 12 may also be placed on a stage 44, which includes a positioning mechanism for moving the stage (and target) relative to the incident beam. By way of examples, one or more motor mechanisms may each be formed from a screw drive and stepper motor, linear drive with feedback position, or band actuator and stepper motor. The system 30 may also include one or more scanning mirrors or other beam movement mechanisms to additionally or alternatively move the probe beam with respect to the target. For instance, the positioning mechanism may cause the probe beam to be directed sequentially to four relative target positions (e.g., for measuring from four different target locations to eliminate $1^{st}$ and $2^{nd}$ orders).

The simultaneous multiple angle approach is not limited to reflectometry. As noted in U.S. Pat. Nos. 5,042,951 and 5,166,752 (incorporated herein by reference), it is also possible to obtain ellipsometric measurements corresponding to $\Psi$ and $\Delta$. simultaneously at multiple angles of incidence. To obtain such measurements, some additional optical elements may be added to the device of FIG. 7. For example, a polarizer 66 (shown in phantom) may be desirable to accurately pre-determine the polarization state of the probe beam. On the detection side, an analyzer 68 (also shown in phantom) may be provided to aid in analyzing the change in polarization state of the probe beam due to interaction with the sample. The optical components of the analyzer can be of any type typically used in an ellipsometer such as a polarizer or a retarder. The ellipsometric output signals are analyzed in a fashion similar to the prior art approaches for using ellipsometric data to evaluate the geometry of periodic structures.

Another approach to increasing the size of the probe beam spot is to use an incoherent source for the probe beam. Such an incoherent source can include a variety of well-known spectral line or broad band sources. If a spectral line light source is used, some modest level of narrow pass filtering may be desirable. Such a filter could be located either before the sample or before the detector as indicated in phantom lines 69a and 69b. The wavelength which is used is selected in order to maximize the sensitivity in the reflection response to the type of changes of interest.

It would also be possible to use a broadband or white light source generating a polychromatic beam. In this situation, the wavelength selective filter could be in the form of a conventional monochrometer. A monochrometer, which typically includes a dispersive element and a slit, functions to transmit a narrow band of wavelengths. The system could be arranged to take measurements at only one wavelength or in a series of sequential wavelengths as the monochrometer is tuned. The use of an incoherent light source would fill the field of view on the sample (typically 100 microns or more for a 0.9 NA microscope objective). The actual measurement spot size is controlled by an aperture that can be varied in size as needed for the particular measurement in question. Such variable spatial filtering is described in U.S. Pat. No. 5,412,473.

It is also within the scope of the subject invention to combine these measurements with other measurements that might be available from a composite tool. For example, these other technologies may include broadband reflectometry and broadband ellipsometry. The output from these additional modules can be used in combination with the BPR signals to more accurately evaluate the geometry of the periodic structures.

The reflected/scattered beam passes back up through the lens 40 which collimates the beam. The reflected beam is redirected by a splitter 46 to an imaging lens 48. Lens 48 magnifies and relays an image of the sample at the focal plane of the lens. A spatial filter 50 having an aperture may be placed in the focal plane of the lens 48 for controlling size of the area of the sample which is measured.

The probe beam may then be passed through a 50-50 splitter and directed to two photodetectors 54 and 56 having a linear array of detector elements. The photodetectors are arranged orthogonal to each other to measure both the S and P polarization components. As described in detail in the above cited patents, each of the detecting elements in the array measure different angles of incidence. The radial position within the reflected probe beam is mapped to the angle of incidence, with the rays closer to the center of the beam having the smallest angles of incidence and the rays in the radially outer portion of the beam corresponding to the greatest angles of incidence. Thus, each detector element simultaneously generates independent signals that correspond to different angles of incidence.

Each detector 54 and 56 may take any suitable form for sensing an optical signal. Each detector may include charged coupled devices (CCD), CCD arrays, time delay integration (TDI) sensors, TDI sensor arrays, photomultiplier tubes (PMT), and other sensors. The detector may be a phase-sensitive detector. The detector may include additional phase compensation devices.

The output signals from the detector arrays may be supplied to processor 60, which may also be coupled with a memory. Processor may generally be configured to analyze the signals based on an algorithm that considers the reflected and scattered light, such as a rigorous coupled wave analysis. The selected algorithm may correlate the variation in reflectivity as a function of angle of incidence with the geometry of the periodic structure. Such scattered light theoretical models are well known in the literature. Those skilled in the art of analyzing signals diffracted from periodic structures will understand that there are many other approaches which can be utilized. Since this system obtains measurements at multiple angles of incidence, higher order diffraction effects may be collected and considered as described herein. The processor and one or more memory (e.g., 60) may also be configured to control the various components of the system 30

Any suitable mechanism may also be used to generate multiple incident beams onto different relative target positions. For instance, a pupil plane module 67 may be configured to produce a desired shape and/or spot separation corresponding to selected relative target positions. Examples of a pupil plane module 77 include an illumination pupil or apodizer, illumination field stop, illumination beam splitter, or illumination grating.

Each target may be designed to follow specific target rules, which preferably include a requirement that the target be placed in a layer which is measurable or inspectable by a particular type of tool. The targets described herein may be placed in any suitable space on the wafer. By way of examples, the targets may be placed in the scribe line or within the dies themselves. When targets are placed in a die, the die layout may also be analyzed to determine whether particular portions or areas have a characteristic which negatively or positively affects metrology results, as compared with other areas of the die layout. For example, particular layout characteristics may result in more reliable or accurate metrology or inspection results. In one specific case, targets may be placed in areas which have characteristics that positively affect the metrology. In an example of such a feature characteristic, a chemical mechanical polishing (CMP) procedure is typically tuned to achieve superior accuracy with a particular feature density range. Thus, targets, such as overlay targets, may be placed in layout regions which are within the particular feature density range for an optimal CMP process.

The circuit designer may be aware of feature locations in the die layout which are most susceptible to error or defects. The designer may communicate the position of such features to the target placement software or layout engineer so that targets may be placed proximate to such problem features. This placement technique would likely result in a higher incidence of defect capture and more reliable resulting products.

The targets may also be placed within a dummy layer. It is common practice in semiconductor manufacturing today to include dummy structures in open areas of the circuit layout to ensure uniform pattern density. Dummy structures are generally used for optimal results in chemical mechanical polishing and other semiconductor manufacturing processes.

In order to enable targets inside the chip area, the functionality of the particular metrology target may be combined with the purpose of the dummy structures. That is, a structure which has two components that serve both purposes of a dummy structure and a metrology (or inspection) target would efficiently utilize the open spaces of the die area to increase CMP uniformity (and other dummy requirements where applicable), as well as to provide a metrology target. Additionally, a new type of metrology may be used with such combination marks. For example, a particular design pattern's fidelity may be monitored via such combination target. That is, a designer's intent regarding a particular pattern's function or structure may be verified with respect to the pattern being combined and measured or inspected in a dummy structure.

The target structures described herein may be generally patterned using suitable photolithographic techniques, and the lithographic patterns are subsequently transferred to other materials and layers using established processing techniques, such as etching and deposition. In the simplest application, the transferred patterns constitute etched or deposited lines or vias. For example, the structures may be formations of photoresist material, recessed cavity formations, embedded trenches and/or other structures within a wafer layer. The structures formed by cavities may be cavities formed in any of the layers during the semiconductor fabrication process. For example, the cavities may be formed in the photoresist layer, the dielectric material layer, or the metal layers. It should be noted that the above processes are not a limitation and that any suitable fabrication technique may be used.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. A method of obtaining optical signal measurements from a periodic semiconductor target, the method comprising:
   selecting one or more zero or non-zero diffraction orders for eliminating corresponding zero or non-zero diffraction order terms from a plurality of measurements from a periodic target using an optical metrology tool, wherein the periodic target has a pitch and the plurality of measurements contain a zero diffraction order term and one or more non-zero diffraction order terms;

using the optical metrology tool, directing an incident beam to a plurality of positions on the target and obtaining the measurements from the target in response to the incident beam being directed to each position; and combining the measurements from the positions of the targets to eliminate each zero or non-zero diffraction order term associated with each selected zero or non-zero diffraction order, resulting in a processed metrology signal, wherein the positions are shifted from each other by a rational fraction of the pitch so as to cause the zero or non-zero diffraction order term corresponding to each selected zero or non-zero diffraction order to be eliminated during the combining of the measurements from the positions.

2. The method of claim 1, further comprising using the processed metrology signal in a model-based metrology process for determining one or more parameters of the target.

3. The method of claim 1, further comprising using the processed metrology signal in a calibration process for the optical metrology tool.

4. The method of claim 1, wherein one or more non-zero diffraction orders are selected and the measurements are processed so that the processed metrology signal retains only zero diffraction order terms and eliminates non-zero diffraction order terms corresponding to the selected one or more non-zero diffraction orders.

5. The method of claim 1, wherein one or more non-zero diffraction orders are selected and the measurements are processed so that the processed metrology signal retains only zero diffraction order terms and separated non-zero diffraction order terms corresponding to the selected one or more non-zero diffraction orders, while eliminating interference terms corresponding to the selected one or more non-zero diffraction orders.

6. The method of claim 1, wherein the measurements are electric field measurements and wherein the measurements are processed so that the processed metrology signal is equal to an average of the electric field measurements from the positions.

7. The method of claim 6, wherein the electric field measurements are obtained in the near-field portion of the optical metrology system.

8. The method of claim 6, wherein the electric field measurements are obtained in the far-field portion of the optical metrology system.

9. The method of claim 6, wherein the average of the electric field measurements is determined by:

$$E_{av}(x) = \frac{1}{2m} \sum_{i=0}^{2*m-1} E_{refl}\left(x + \frac{i}{2m} \text{Pitch}\right),$$

wherein m equals a highest one of the selected one or more zero or non-zero diffraction orders and x corresponds to a first one of the positions.

10. The method of claim 1, wherein each relative shift between the positions is selected based on the selected one or more zero or non-zero diffraction orders, while an absolute value for each position is unspecified.

11. The method of claim 1, wherein the positions are shifted with respect to each other by a rational fraction of the pitch based on the selected one or more zero or non-zero diffraction orders.

12. The method of claim 1, wherein the measurements include a spatial average of a plurality of sub-measurements for each position.

13. The method of claim 1, wherein the target comprises gratings arranged in two directions.

14. The method of claim 1, wherein the measurements are obtained using a plurality of incident beams directed simultaneously to at least two of the positions.

15. The method of claim 1, wherein one or more non-zero diffraction orders are selected and the measurements are processed so that the processed metrology signal retains only zero diffraction order terms and one or more non-zero diffraction order terms not corresponding to the selected one or more diffraction orders and eliminates non-zero diffraction order terms corresponding to the selected one or more diffraction orders.

16. The method of claim 1, wherein the measurements are processed so that the processed measurement signal retains an individual interference term corresponding to one of the selected one or more zero or non-zero diffraction orders and such individual interference term is retained by comparing the plurality of measurements to each other.

17. A method of obtaining optical signal measurements from a periodic semiconductor target, the method comprising:

selecting one or more zero or non-zero diffraction orders for eliminating or obtaining corresponding zero or non-zero diffraction order terms from a plurality of measurements from a periodic target using an optical metrology tool, wherein the periodic target has a pitch and the plurality of measurements contain a zero diffraction order term and one or more non-zero diffraction order terms;

using the optical metrology tool, directing an incident beam to a plurality of positions on the target and obtaining the measurements from the target in response to the incident beam being directed to each position; and combining the measurements from the positions of the targets to eliminate each zero or non-zero diffraction order term associated with each selected zero or non-zero diffraction order, resulting in a processed metrology signal, wherein the positions are shifted from each other by a rational fraction of the pitch so as to cause the zero or non-zero diffraction order term corresponding to each selected zero or non-zero diffraction order to be eliminated during the combining of the measurements from the positions, wherein the measurements are intensity measurements and wherein the measurements are processed so that the processed metrology signal is equal to an average of the intensity measurements from the positions.

18. The method of claim 17, wherein the average of the intensity measurements is determined by:

$$I_{av}(x) = \frac{1}{2m} \sum_{i=0}^{2*m-1} I\left(x + \frac{i}{2m} \text{Pitch}\right)$$

wherein m equals a highest one of the selected one or more zero or non-zero diffraction orders and x corresponds to a first one of the positions.

19. An apparatus for obtaining optical signal measurements from a periodic semiconductor target, comprising:

a light source and lens system for generating and directing an incident beam towards a periodic target having a pitch;

a plurality of scanning mirrors or positioning mechanisms for moving the periodic target with respect to the incident beam so that the incident beam is directed to a plurality of positions on the periodic target;

one or more detectors for obtaining a plurality of measurements having multiple diffraction orders from the plurality of positions of the periodic target in response to the incident beam, wherein the plurality of measurements contain a zero diffraction order term and one or more non-zero diffraction order terms, and wherein the positions are shifted from each other by a rational fraction of the pitch so as to cause the zero or non-zero diffraction order term corresponding to each selected zero or non-zero diffraction order to be eliminated during combining of the measurements from the positions; and a processor configured to perform the following operations:

selecting one or more zero or non-zero diffraction orders for eliminating corresponding zero or non-zero diffraction order terms from the plurality of measurements from the periodic target;

combining the measurements from the positions of the targets to eliminate each zero or non-zero diffraction order term associated with each selected zero or non-zero diffraction order, resulting in a processed metrology signal.

20. The apparatus of claim 19, wherein the processor is further operable to analyze the processed metrology signal in a model-based metrology process to determine one or more parameters of the target.

21. The apparatus of claim 20, wherein the processor is further operable to analyze the processed metrology signal in a calibration process to calibrate the optical metrology tool.

22. The apparatus of claim 19, wherein one or more non-zero diffraction orders are selected and the measurements are processed so that the processed metrology signal retains only zero diffraction order terms and eliminates non-zero diffraction order terms corresponding to the selected one or more non-zero diffraction orders.

23. The apparatus of claim 19, wherein one or more non-zero diffraction orders are selected and the measurements are processed so that the processed metrology signal retains only zero diffraction order terms and separated non-zero diffraction order terms corresponding to the selected one or more non-zero diffraction orders, while eliminating interference terms corresponding to the selected one or more non-zero diffraction orders.

24. The apparatus of claim 19, wherein the measurements are electric field measurements and wherein the measurements are processed so that the processed metrology signal is equal to an average of the electric field measurements from the positions.

25. The apparatus of claim 19, wherein the measurements are intensity measurements and wherein the measurements are processed so that the processed metrology signal is equal to an average of the intensity measurements from the positions.

* * * * *